United States Patent
Bubalo

(10) Patent No.: US 7,930,840 B1
(45) Date of Patent: Apr. 26, 2011

(54) TOE PROTECTION APPARATUS

(76) Inventor: Charles E. Bubalo, McComb, OH (US)

( * ) Notice: Subject to any disclaimer, the term of this patent is extended or adjusted under 35 U.S.C. 154(b) by 665 days.

(21) Appl. No.: 12/045,887

(22) Filed: Mar. 11, 2008

(51) Int. Cl.
*A43C 13/14* (2006.01)

(52) U.S. Cl. .......................... 36/77 R; 36/72 R

(58) Field of Classification Search ............... 36/77 R, 36/77 M, 72 R, 7.2, 7.4, 7.7
See application file for complete search history.

(56) References Cited

U.S. PATENT DOCUMENTS

| | | | | |
|---|---|---|---|---|
| 1,640,669 A | * | 8/1927 | Sankey | 36/72 R |
| 1,952,294 A | * | 3/1934 | Strauss | 36/72 R |
| 2,160,768 A | * | 5/1939 | Wasser | 36/72 R |
| 2,339,193 A | * | 1/1944 | Roberts | 36/72 R |
| 2,392,867 A | * | 1/1946 | Stoner et al. | 36/72 R |
| 2,436,187 A | * | 2/1948 | Bestland | 36/72 R |
| 2,644,249 A | * | 7/1953 | Stern | 36/7.5 |
| 3,128,565 A | * | 4/1964 | Graham et al. | 36/2 R |
| 3,271,888 A | * | 9/1966 | Graham et al. | 36/72 R |
| 3,834,377 A | | 9/1974 | Lebold | |
| 4,177,583 A | | 12/1979 | Chapman | |
| 4,237,628 A | * | 12/1980 | Etancelin | 36/131 |
| 4,414,759 A | | 11/1983 | Morgan et al. | |
| 5,483,757 A | | 1/1996 | Frykberg | |
| 5,694,703 A | * | 12/1997 | Diaz | 36/7.1 R |
| 5,778,565 A | | 7/1998 | Holt et al. | |
| 5,926,978 A | | 7/1999 | Smith | |
| D438,972 S | | 3/2001 | Darby | |
| 6,272,771 B1 | | 8/2001 | Rodi | |
| 6,981,340 B2 | * | 1/2006 | Evans | 36/7.2 |
| D534,712 S | | 1/2007 | Darby, II | |

* cited by examiner

*Primary Examiner* — Marie Patterson
(74) *Attorney, Agent, or Firm* — Crossley Patent Law; Mark A. Crossley

(57) ABSTRACT

A toe protection apparatus for use with a foot or footwear, featuring a rounded steel toe cover with cushioning liner affixed within, a bracket affixed to the top of the steel toe cover, a housing fastened to the bracket, the housing surrounding the steel toe cover and the bracket, the housing further comprising a housing top, a rounded front, opposite vertical sides, and a housing bottom, the housing bottom coplanar with the steel toe cover bottom, a hook and loop affixed to the housing top and the rounded front, an adjustably fastened under foot strap for encircling the housing top and housing sides and the foot or footwear of a user, an adjustably fastened heel strap for encircling a foot heel or a footwear heel and the rounded front of the housing.

9 Claims, 6 Drawing Sheets

TOE PROTECTION APPARATUS

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

Be it known that I, Charles E. Bubalo, a citizen of the United States, have invented new and useful improvements in a toe protection apparatus as described in this specification.

BACKGROUND OF THE INVENTION

Often, prior to or after medical procedures on a foot, use of normal footwear is not possible or recommended. A walking boot, often termed an orthopedic shoe, or open-toed shoe or even sandals are prescribed for use by a patient for a period of time. Hampered mobility is not the only issue in such instances. For example, if such patients happen to be hard hat workers, job attendance is not possible due to increased chance of foot and especially toe injury, as the typically worn and mandated protective footwear cannot be used. Mandated footwear on countless job sites includes steel toe protection. Lost worker time and the associated costs are therefore a reality that is unwelcome by the employee and employer. What has been needed is a toe protection device which can be used with various forms of footwear, whether medically oriented or otherwise. The device should also be usable even without footwear, as foot protection may be needed even when footwear is removed.

Such a device should be easily applied and removed and should provide steel-toed protection against toe injury. The device should be basic and easily adjustable for fit. The present apparatus provides for these needs.

FIELD OF THE INVENTION

The toe protection apparatus relates to toe protection and more especially to a toe protection apparatus for use with orthopedic foot supports and other footwear from which a user benefits from toe protection, or even for use without footwear.

SUMMARY OF THE INVENTION

The general purpose of the toe protection apparatus, described subsequently in greater detail, is to provide a toe protection apparatus which has many novel features that result in an improved toe protection apparatus which is not anticipated, rendered obvious, suggested, or even implied by prior art, either alone or in combination thereof.

To attain this, the toe protection apparatus provides steel toe protection, whether a user wears or does not wear footwear. The apparatus further provides for easy, adjustable fit, with hook and loop in strategic locations for best access in attachment and removal. The steel toe cover is housed within the housing, which features a flat top, vertical sides, and a rounded front. Vertical sides of the housing enhance strength and insure adequate clearance for toes, and protection.

The steel toe cover itself has a bottom that is coplanar with that of the housing bottom, for assured toe protection. The toe cover further features a cushioning liner for protection of feet and of footwear. The apparatus provides protection so that activities not normally available become so, whether in work situations or in relaxation. Although not limited to such, the housing is ideally of a synthetic material such as plastic. The apparatus is provided in a plurality of sizes, and appropriate under foot straps and heel straps are provided with each size. The apparatus is basic so that economy of production and sales are provided.

Thus has been broadly outlined the more important features of the improved toe protection apparatus so that the detailed description thereof that follows may be better understood and in order that the present contribution to the art may be better appreciated.

An object of the toe protection apparatus is to provide steel toe protection, that can be used with or without footwear.

A further object of the toe protection apparatus is to be easily fitted and removed.

An added object of the toe protection apparatus is to be adjustably fitted.

These together with additional objects, features and advantages of the improved toe protection apparatus will be readily apparent to those of ordinary skill in the art upon reading the following detailed description of presently preferred, but nonetheless illustrative, embodiments of the improved toe protection apparatus when taken in conjunction with the accompanying drawings.

In this respect, before explaining the current embodiments of the improved toe protection apparatus in detail, it is to be understood that the toe protection apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved toe protection apparatus. It is therefore important that the claims be regarded as including such equivalent constructions insofar as they do not depart from the spirit and scope of the toe protection apparatus. It is also to be understood that the phraseology and terminology employed herein are for purposes of description and should not be regarded as limiting.

DETAILED DESCRIPTION OF THE DRAWINGS

With reference now to the drawings, and in particular FIGS. 1 through 7 thereof, the principles and concepts of the toe protection apparatus generally designated by the reference number 10 will be described.

Figure 1:
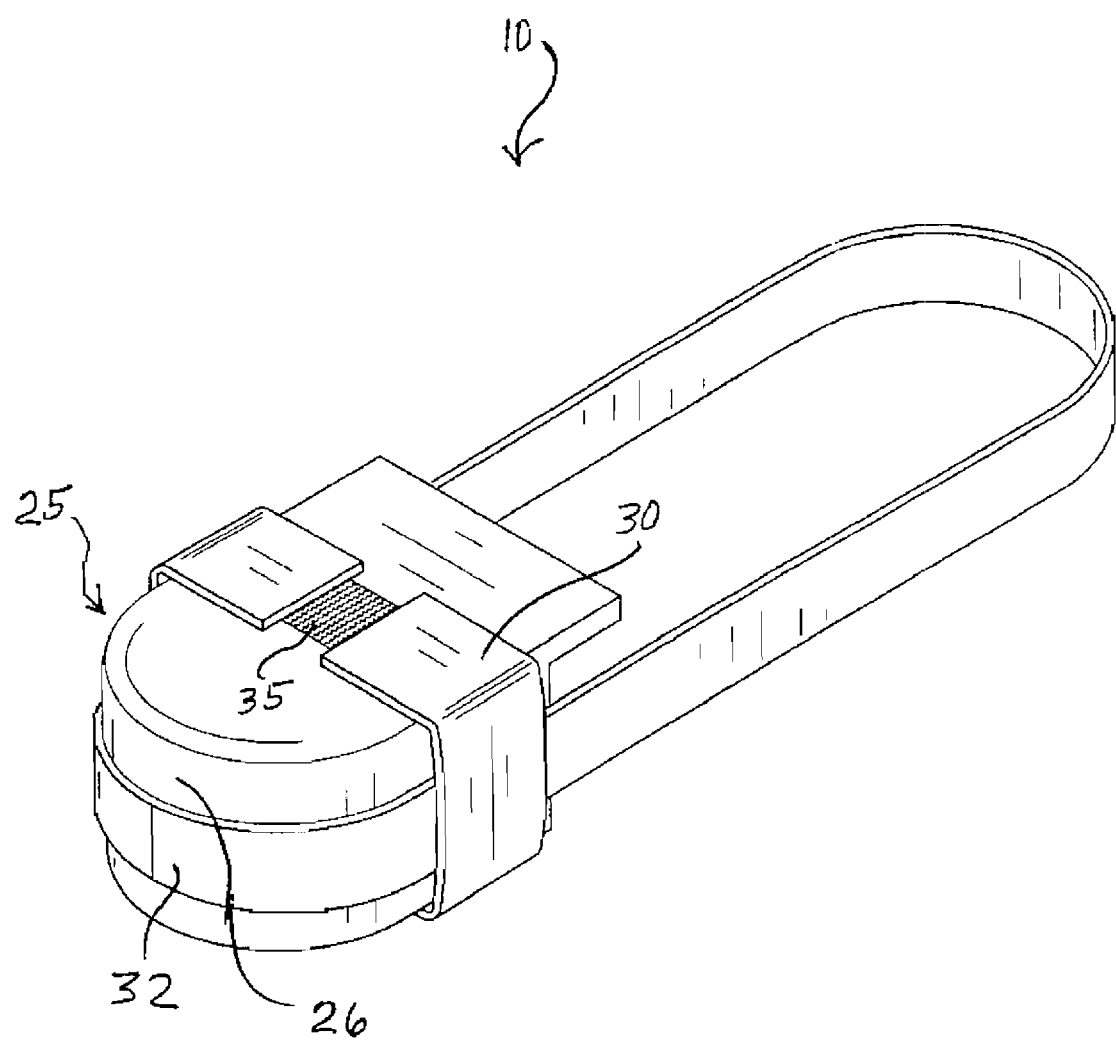
FIG. 1 is a perspective view.
Figure 2:
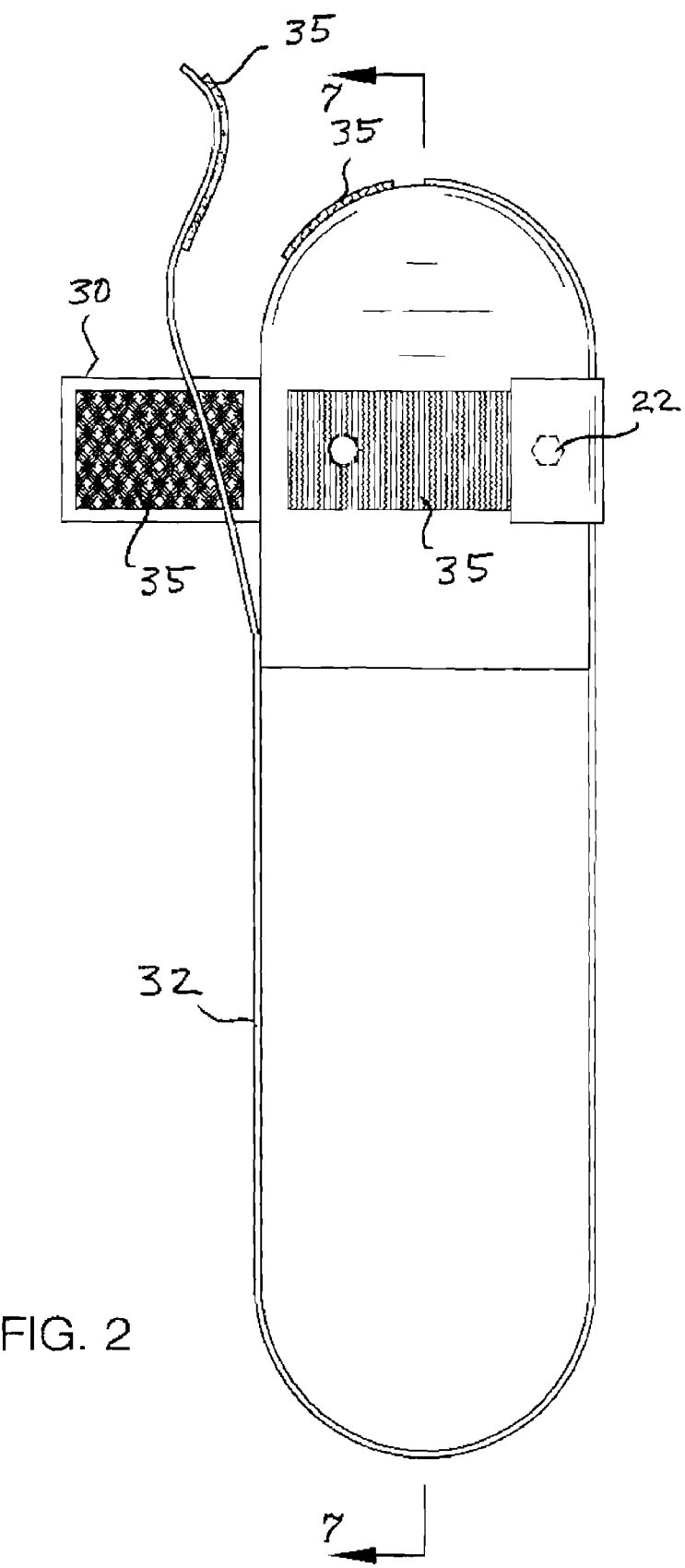
FIG. 2 is a top plan view.
Figure 3:
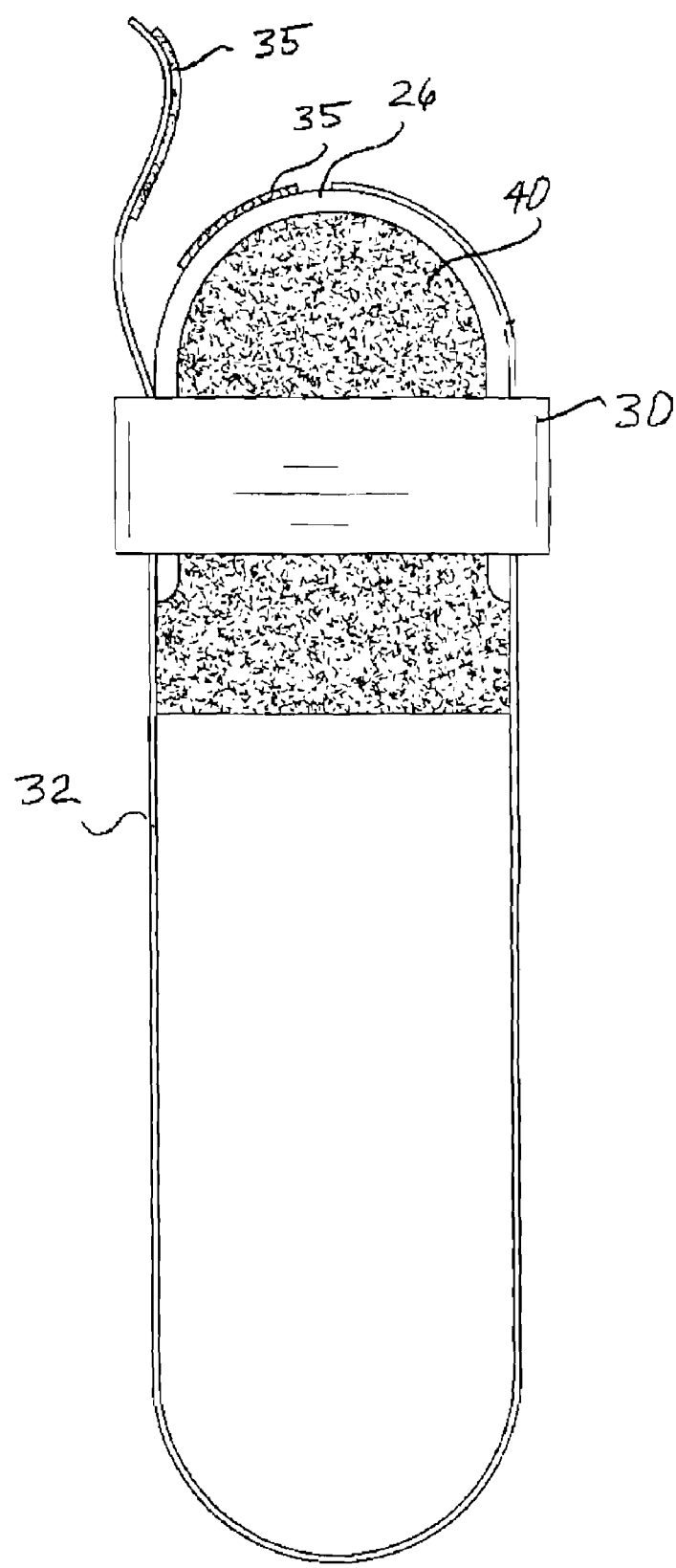
FIG. 3 is a bottom plan view.
Figure 4:
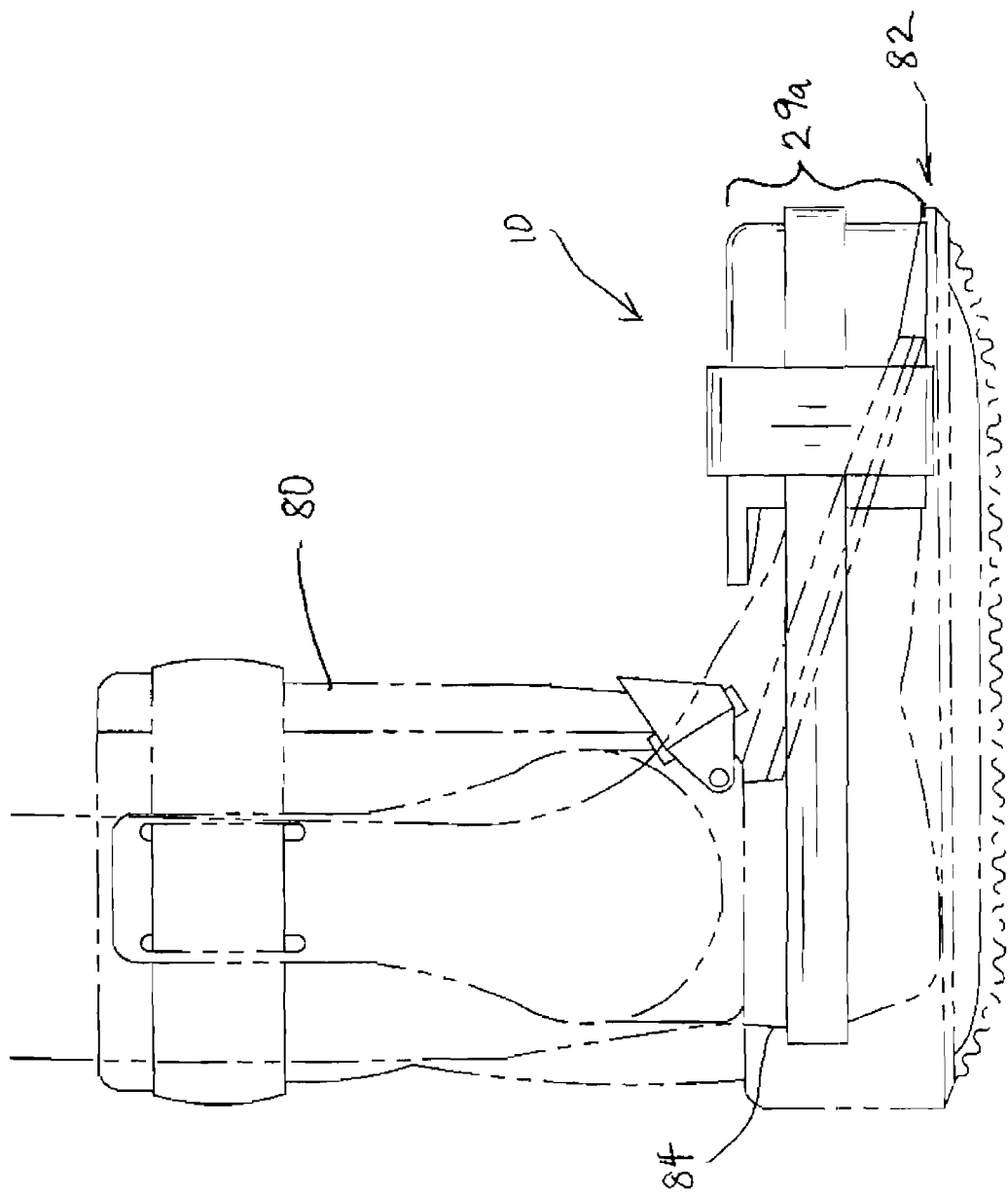
FIG. 4 is a lateral elevation view of the apparatus in use with a walking boot.
Figure 5:
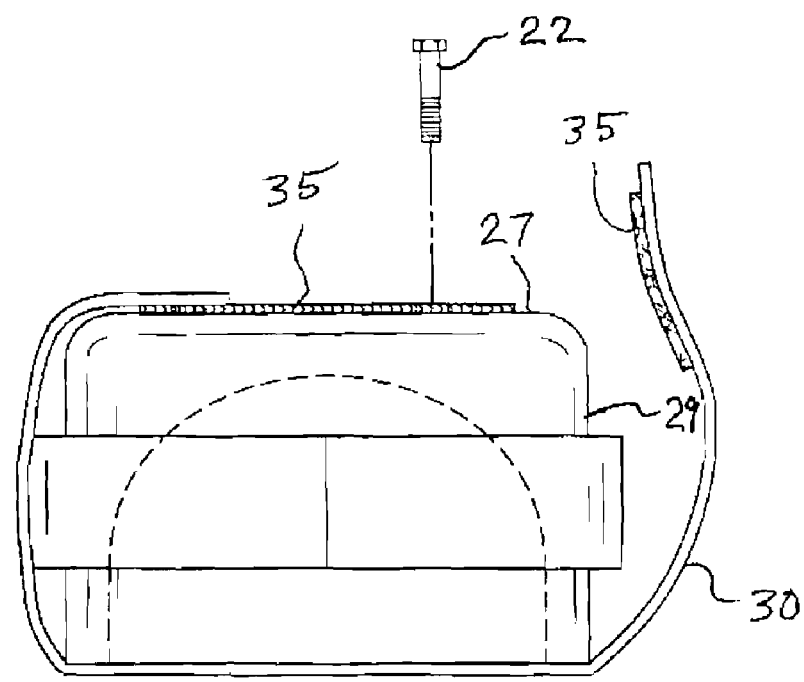
FIG. 5 is a front elevation view.
Figure 6:
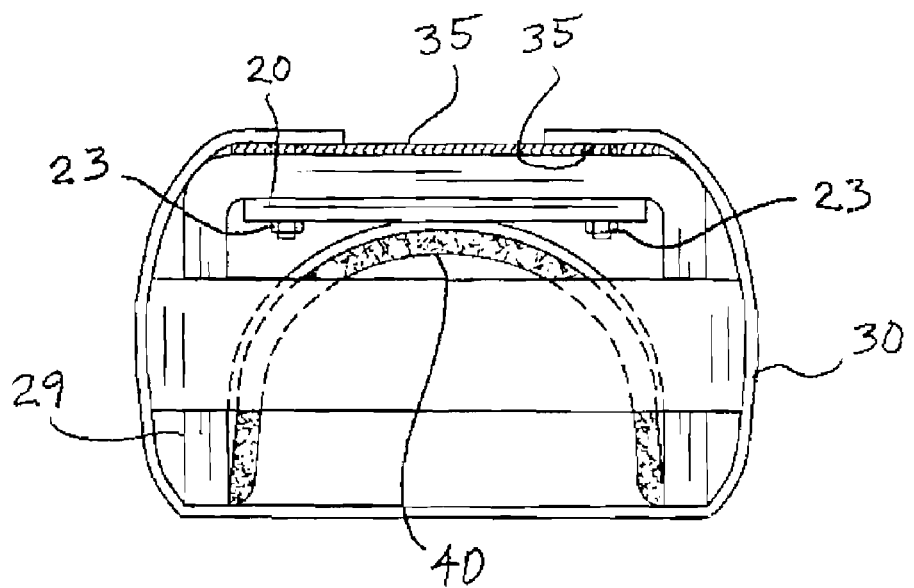
FIG. 6 is a front cross sectional view.
Figure 7:
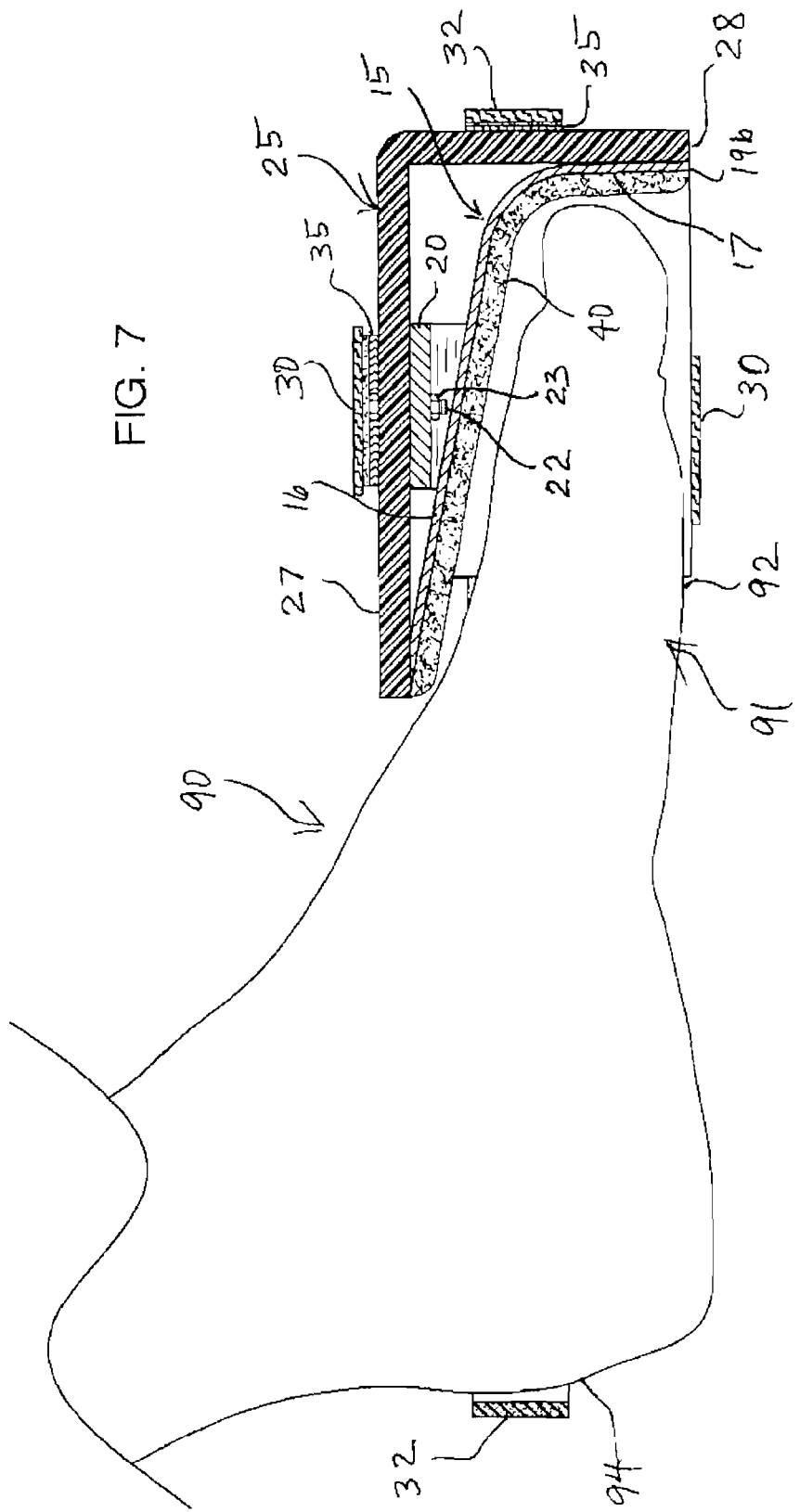
FIG. 7 is a lateral cross sectional view of the apparatus in use.

Referring to FIGS. 1, 4 and 7, the toe protection apparatus 10 is provided for use with a foot 90 or with footwear 80, such as the walking boot illustrated. The apparatus 10 is not confined to one size but is instead provided in a plurality of sizes to fit various feet 90 and footwear 80. The housing side heights 29a of the housing sides 29 extend to the housing bottom 28 which is level with that of the foot bottom 92, thereby affording full shielding of forefoot top and sides 91. The housing sides 29 are also provided in embodiments wherein housing side heights 29a are level with that of footwear bottom 82 of footwear 80, thereby shielding footwear 80. Continuing to refer to FIG. 7 and further referring to FIGS. 2, 3, 5, and 6, the apparatus 10 further comprises the rounded steel toe cover 15 having an angled top 16 seamlessly and gradually joined to a vertical front 17. The toe cover 15 further comprises a cover bottom 19b.

The cushioning liner 40 is affixed within the steel toe cover 15 and acts to protect either a foot 90 or footwear 80. The bracket 20 is affixed to the top 16 of the steel toe cover 15. The housing 25 is fastened to the bracket 20 via bolts 22 and nuts 23. The housing 25 surrounds the steel toe cover 15 and the bracket 20. The housing 25 further comprises a housing top 27, a rounded front 26, opposite vertical housing sides 29, and a housing bottom 28, the housing bottom 28 coplanar with the steel toe cover bottom 19b. Vertical housing sides 29 insure strength and adequate foot 90 and footwear 80 clearance. Hook and loop 35 is affixed to the housing top 16 and also to the rounded front 26. The adjustably fastened under foot strap 30 is for encircling the housing top 27 and housing sides 29 and the foot 90 or footwear 80 of a user. The under foot strap 30 further comprises hook and loop 35 for removable attachment to the complimentary hook and loop 35 of the housing top 27. The adjustably fastened heel strap 32 is provided for encircling the foot heel 94 or the footwear heel 84 and the rounded front 26 of the housing 25. The heel strap 32 further comprises hook and loop 35 for removable attachment to the hook and loop 35 of the rounded front 26.

With respect to the above description then, it is to be realized that the optimum dimensional relationships for the parts of the toe protection apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the toe protection apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the toe protection apparatus may be used.

Therefore, the foregoing is considered as illustrative only of the principles of the toe protection apparatus. Further, since numerous modifications and changes will readily occur to those skilled in the art, it is not desired to limit the toe protection apparatus to the exact construction and operation shown and described, and accordingly, all suitable modifications and equivalents may be resorted to, falling within the scope of the toe protection apparatus.

What is claimed is:

1. A toe protection apparatus, comprising:
    a rounded steel toe cover having a top seamlessly joined to a front;
    a bracket affixed to the top of the steel toe cover;
    a housing fastened to the bracket, the housing surrounding the steel toe cover and the bracket, the housing further comprising a housing top, opposed vertical housing sides, and a housing front;
    an adjustably fastened under foot strap whereby the under foot strap encircles the housing top and sides and a foot or a footwear of a user;
    an adjustably fastened heel strap for encircling a foot heel or a footwear heel and the housing front.

2. The apparatus according to claim 1 further comprising a cushioning liner affixed within the steel toe cover.

3. The apparatus according to claim 1 wherein the housing sides further comprise housing side heights of the housing sides extending to a housing bottom wherein the housing bottom is level with that of a foot bottom, thereby shielding the entire forefront top and sides.

4. A toe protection apparatus for use with a foot or footwear, comprising:
    a rounded steel toe cover having a top seamlessly joined to a front, the toe cover further comprising a cover bottom;
    a bracket affixed to the top of the steel toe cover;
    a housing fastened to the bracket, the housing surrounding the steel toe cover and the bracket, the housing further comprising a housing top, opposed housing sides, a housing front, and a housing bottom coplanar with the steel toe cover bottom;
    an adjustably fastened under foot strap for encircling the housing top and sides and the foot or footwear of a user;
    an adjustably fastened heel strap for encircling a foot heel or a footwear heel and the housing front.

5. The apparatus according to claim 4 further comprising a cushioning liner affixed within the steel toe cover.

6. The apparatus according to claim 5 wherein the housing sides further comprise vertical sides.

7. The apparatus according to claim 6 wherein the housing sides further comprise shielding for an entire forefoot top and sides.

8. A toe protection apparatus for use with a foot or footwear, comprising:
    a rounded steel toe cover having an angled top seamlessly joined to a vertical front, the toe cover further comprising a cover bottom;
    a cushioning liner affixed within the steel toe cover;
    a bracket affixed to the top of the steel toe cover;
    a housing fastened to the bracket, the housing surrounding the steel toe cover and the bracket, the housing further comprising a housing top, a rounded front, opposite vertical sides, and a housing bottom, the housing bottom coplanar with the steel toe cover bottom;
    a hook and loop affixed to the housing top and the rounded front;
    an adjustably fastened under foot strap for encircling the housing top and housing sides and the foot or footwear of a user, the under foot strap further comprising hook and loop for removable attachment to the hook and loop of the housing top;
    an adjustably fastened heel strap for encircling a foot heel or a footwear heel and the rounded front of the housing, the heel strap further comprising hook and loop for removable attachment to the hook and loop of the rounded front.

9. The apparatus according to claim 8 wherein the housing sides further comprise shielding for an entire forefoot top and sides.

* * * * *